United States Patent [19]

Shanklin, Jr. et al.

[11] Patent Number: 5,130,309

[45] Date of Patent: Jul. 14, 1992

[54] ARYLOXY AND ARYLOXYALKLAZETIDINES AS ANTIARRHYTHMIC AND ANTICONVULSANT AGENTS

[75] Inventors: James R. Shanklin, Jr., Richmond, Va.; Mark R. Hellberg, Arlington, Tex.

[73] Assignee: A. H. Robins Company, Incorporated, Richmond, Va.

[21] Appl. No.: 684,313

[22] Filed: Apr. 12, 1991

[51] Int. Cl.$^5$ ................ A61K 31/395; C07D 205/04
[52] U.S. Cl. .................................. 514/210; 548/950; 548/952
[58] Field of Search ............ 514/210; 548/950, 952

[56] References Cited

U.S. PATENT DOCUMENTS

| | | | |
|---|---|---|---|
| 3,983,245 | 9/1976 | Ladd | 424/285 |
| 4,226,861 | 10/1980 | Cale | 424/244 |
| 4,379,151 | 4/1983 | Cale | 548/952 X |
| 4,379,167 | 4/1983 | Lunsford | 424/330 |
| 4,505,907 | 3/1985 | Wright | 514/210 |
| 4,571,393 | 2/1986 | Teng | 514/210 |
| 4,806,555 | 2/1989 | Lunsford | 514/652 |
| 4,956,359 | 9/1990 | Taylor | 514/210 |

OTHER PUBLICATIONS

Rodebaugh, R. M. and Cromwell, N. H. J. Het Chem. 8, 19-24 (1971).
Okutani, T.; Kaneko, T. and Masuda, K. Chem. Pharm. Bull. 22(7), 1490-1497 (1974).

*Primary Examiner*—Robert W. Ramsuer
*Assistant Examiner*—Jacqueline Haley
*Attorney, Agent, or Firm*—Robert F. Boswell, Jr.

[57] ABSTRACT

Methods of treating cardiac arrhythmias and convulsions in warm-blooded animas and pharmaceutical compositions therefor are disclosed. The compounds useful in the methods of treatment and compositions are represented by the formula

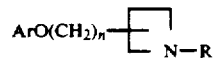

where n is 0 to 3 and R is H, $C_1$-$C_4$ alkyl or arylalkyl and Ar is phenyl or substituted phenyl.

6 Claims, No Drawings

ARYLOXY AND ARYLOXYALKLAZETIDINES AS ANTIARRHYTHMIC AND ANTICONVULSANT AGENTS

BACKGROUND OF THE INVENTION

This invention relates to the antiarrhythmic and anticonvulsant properties of 2- and 3-aryloxy or aryloxyalkyl azetidines. The compounds of this invention have the azetidine nitrogen substituted by hydrogen, loweralkyl or arylalkyl.

Anticonvulsant activity has been observed for 3-aryloxazetidines which have the formula:

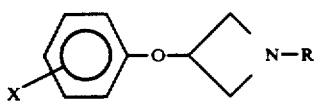

and where X and R are further defined hereinbelow. U.S. Pat. No. 4,226,861 discloses anticonvulsant activity compounds where R is

Compounds having anticonvulsant activity where R is

and X is hydrogen, fluorine, loweralkyl, loweralkoxy, trifluoromethyl, acetyl, or aminocarbonyl are disclosed in U.S. Pat. No. 4,571,393. Anticonvulsant activity is also disclosed for compounds wherein R is N-formylaminocarbonyl or hydroxymethylaminocarbonyl in U.S. Pat. No. 4,505,907. Compounds of the formula:

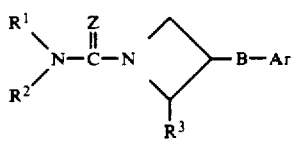

where B and Z are independently O or S; Ar is pyridinyl, halogen-substituted pyridinyl, phenyl or substituted phenyl; $R^1$ and $R^2$ is selected from H, loweraliphatic, cycloalkyl, arylloweralkyl, diloweralkylaminoloweralkyl, or $R^1NR^2$ forms a heterocyclic ring; and $R^3$ is H, loweralkyl, aryl, or arylloweralkyl are disclosed in U.S. Pat. No. 4,956,359 as having anticonvulsant properties.

Azetidine derivatives useful in treating angina and hypertension are disclosed in U.S. Pat. No. 3,983,245 which described compounds having the formula:

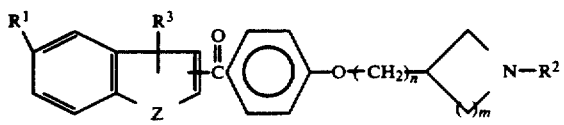

where n is 1 or 0, m is 1-4, Z is O or S and $R^2$ is loweralkyl which are useful as coronary vasodilating agents. In contrast to the above-mentioned disclosures, the anticonvulsant and antiarrhythmic compounds of the present invention do not possess the 1-carboxamido group or derivatives thereof nor is the planar aromatic heterocyclic substituent on the phenoxy moiety necessary for the anticonvulsant or cardiovascular properties described hereinabove.

SUMMARY OF THE INVENTION

The compounds useful as antiarrhythmic and anticonvulsant agents are represented by Formula I below wherein n is 0 to 3,

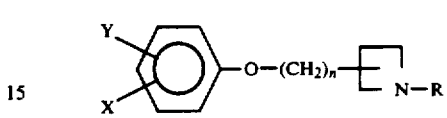

Formula I

R is hydrogen, $C_1$-$C_4$ alkyl, or arylalkyl; X is selected from the group consisting of hydrogen, halogen, trifluoromethyl, $C_1$-$C_4$ alkyl, $R^1O-$, $R^1_2N$,

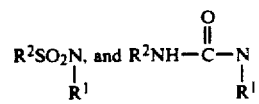

wherein $R^1$ is H, $C_1$-$C_4$ alkyl, or phenyl and $R^2$ is $C_1$-$C_4$ alkyl or phenyl; and Y is hydrogen or $C_1$-$C_4$ alkyl with a proviso that when n is 0, the aryloxy group is attached to the 3 position of azetidine only. Also encompassed under Formula I are the pharmaceutically acceptable salts and stereoisomers where they exist.

Certain terms used in the above description of Formula I compounds are defined hereinbelow.

The term $C_1$-$C_4$ alkyl includes straight and branched hydrocarbon chains and thus encompasses methyl, ethyl, propyl, 2-propyl, butyl, isobutyl, secbutyl, and tertiary butyl. Halogen includes fluorine, chlorine, bromine, and iodine. Arylalkyl is phenyl attached to $C_1$-$C_4$ alkyl such as benzyl or phenylethyl. Pharmacuetically acceptable salt includes solvates, hydrates and nontoxic acid addition salts formed from inorganic and organic acids such as hydrochloric, hydrobromic, sulfuric, phosphoric, fumaric, maleic, tartaric, hexamic, citric, succinic, methanesulfonic acids and the like. Stereoisomers are possible where the aryloxyalkyl group is attached at the 2-position of the azetidine ring.

The compounds of the present invention corresponding to the formula: wherein n is 1 to 3 and Ar and R are as defined above are novel.

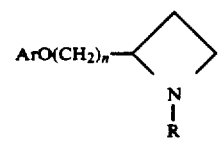

Compounds of this invention have shown antiarrhythmic activity against coronary occlusion induced arrhythmia in dogs and anticonvulsant activity against electrical shock-induced convulsions.

DETAILED DESCRIPTION OF THE INVENTION

Compounds useful in the methods and composition of this invention having the structure of Formula I are prepared according to the following reaction schemes.

Scheme 1.
Displacement of fluorine on an aromatic ring.

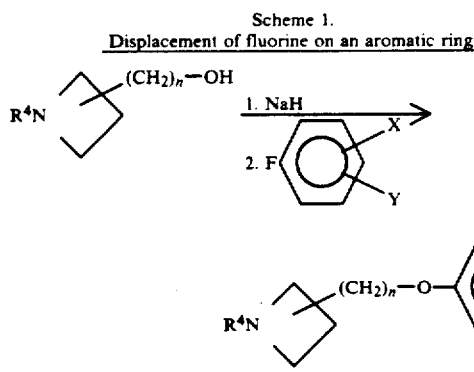

Compounds where X and Y are not electron-donating groups can be prepared by this procedure. $R^4$ is $C_1$-$C_4$ alkyl or phenyl-($C_1$-$C_4$)alkyl or diphenylmethyl. The group $R^4$ when benzyl, 1-phenylethyl or diphenylmethyl can be removed by standard laboratory procedures such as catalytic hydrogenolysis where desired after the aromatic fluorine displacement reaction. The resulting aryloxyalkylazetidine is N-acylated with an appropriate acyl halide followed by reduction with lithium aluminum hydride to obtain a Formula 1 compound. N,N-Dimethylformamide (DMF) is the most often used solvent in reaction scheme 1. This procedure is used in U.S. Pat. No. 4,379,151.

Scheme 2.
Displacement of Leaving Group by Phenoxide

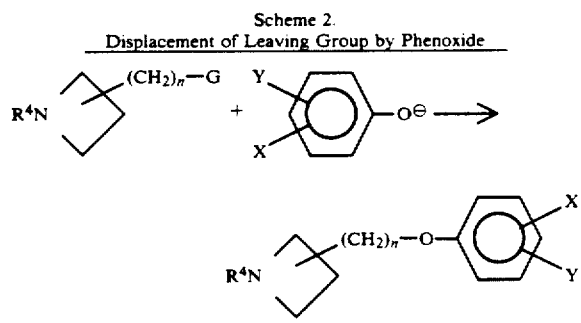

In Scheme 2, the group G, a leaving group such as halogen or the mesylate, benzenesulfonate, or tosylate ester of the corresponding 3-azetidinol or 2- or 3-azetidinyl alkanol, is displaced in a nucleophilic substitution reaction with a phenoxide generated from a phenol and base. An example of this procedure is given in U.S. Pat. No. 4,505,907. This reaction can also be carried out under phase-transfer reaction condition as disclosed in U.S. Pat. No. 4,594,189.

Scheme 3.
Cyclization of 4-aryloxy-3-hydroxybutanamine

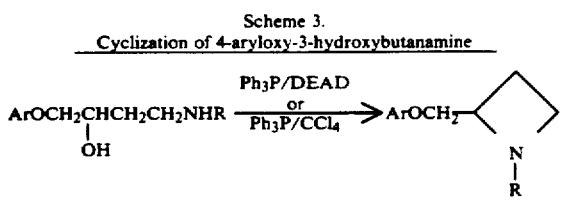

The cyclization reaction of Scheme 3 is described by Sammes and Smith in Journal of the Chemical Society, Chemical Communications 1983, 682-684. Suitable 4-aryloxy-3-hydroxybutylamine intermediates can be prepared as described in U.S. Pat. No. 4,379,167.

Intermediate 1-substituted 3-azetidinols are known. The 3-azetidinols are conveniently prepared according to Scheme 4 from epichlorohydrin and a primary amine, preferably a bulky amine such as isopropylamine or t-butylamine or one that can be removed by catalytic hydrogenation if desired such as benzylamine, benzhydrylamine, or 1-phenylethylamine.

Scheme 4.

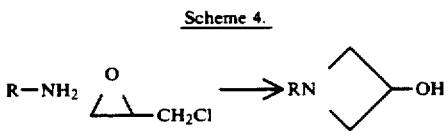

It is difficult to prepare the 1-substituted-3-azetidinols where the substituent is non-bulky, i.e., methyl or ethyl, by the above procedure. However, such azetidinol derivatives can be prepared according to the procedure outlined in Scheme 5.

Scheme 5.

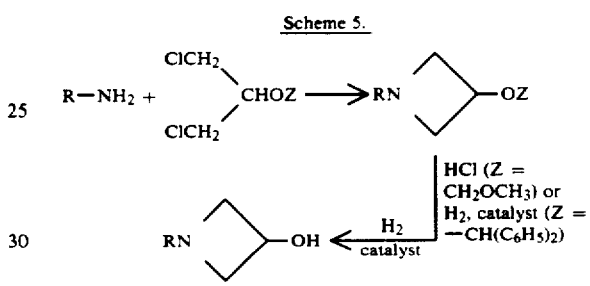

1-Substituted-3-azetidinemethanols can be prepared from 1-substituted-3-azetidinols as indicated in the following reaction sequence.

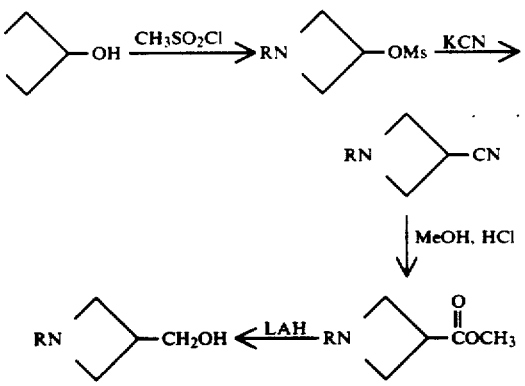

1-Substituted-2-azetidinemethanols are prepared by (1) hydrolysis of 1-benzhydryl-2-cyanoazetidine to the corresponding carboxylic acid and reduction with lithium aluminum hydride or (2) reduction of a directly formed 1-substituted azetidine-2-carboxylic acid ester to give the corresponding azetidine-2-methanol. 1-Benzhydryl-2-azetidinemethanol is converted to 1-benzhydryl-2-azetidineacetic acid by the procedures given in U.S. Pat. No. 4,620,866. Reduction with an appropriate reducing agent such as lithium aluminum hydride gives the corresponding 1-benzhydrylazetidine-2-ethanol. Repetition of the reaction sequence used to obtain the azetidine ethanol is expected to yield the azetidine propanol. Analogously, the azetidine 3-ethanol and azetidine-3-propanol are obtained starting with the 1-substituted-3-azetidine methanol. The reaction sequence used to extend the alkanol chain is the same as shown immediately above where the azetidinol is converted to the azetidine methanol, that is, formation of mesylate ester, displacement with cyanide, hydrolysis, and reduction. Another synthetic method which could be used would be displacement of the mesylate or other leaving group formed from an azetidinol or azetidine methanol with the carbanion formed from a malonic acid ester, hydrolysis of the substituted malonic ester with methanolic HCl, followed by reduction of the resulting monoester with a reducing agent such as lithium aluminum hydride, to obtain an alcohol in which the carbon chain has been extended by two carbons. The reaction scheme is outlined below.

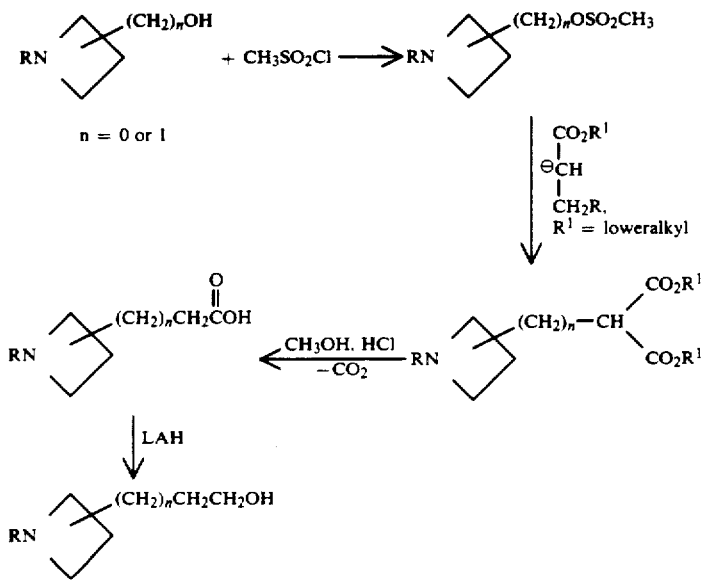

Still other methods of preparation of the intermediate azetidinealkanols and the invention compounds will be apparent to those skilled in the art. The above reaction schemes are broadly disclosed and are in no way limiting to the disclosure of this invention. The following preparations and examples are illustrative of the procedures outlined hereinabove and other methods of preparation will be apparent to one skilled in the art.

PREPARATION 1

1-(Diphenylmethyl)-3-azetidinol methanesulfonate (ester) hydrochloride

A mixture of 60.02 g (0.22 mole) of 1-diphenylmethyl-3-azetidinol hydrochloride and 48.94 g (0.484 mole) of triethylamine in 800 mL of toluene was stirred for 24 hrs, then cooled to 5° C. in an ice bath and treated with 27.7 g (0.24 mole) of methanesulfonyl chloride added at a rate which maintained the temperature below 15° C. The reaction was stirred for 3 hrs. and filtered to remove the triethylamine hydrochloride. The filtrate was treated with 40 g (0.242 mole) of 4-trifluoromethylphenol followed by 19.35 g (0.484 mole) of sodium hydroxide and 1.6 g (0.005 mole) of tetrabutylammonium bromide in 60 mL of water. The reaction mixture was stirred rapidly at reflux for 18 hrs., then stirred for 72 hrs. at ambient temperature. The reaction mixture was transferred to a separatory funnel and washed with 4×200 mL of H$_2$O. The toluene layer was dried over MgSO$_4$ and concentrated in vacuo to an oil (82 g). This residue was dissolved in 200 mL 2-propanol and treated with 20 mL of concentrated hydrochloric acid. Upon cooling, a solid separated and was removed by filtration (5.1 g). Recrystallization from isopropyl alcohol gave 3.3 g of fine white crystalline material, mp 172°-173° C.

Analysis: Calculated for C$_{17}$H$_{19}$NO$_3$S•HCl: C, 57.70; H, 5.70; N, 3.96. Found: C, 57.80; H, 5.86; N, 3.92.

PREPARATION 2

3-Phenoxy-1-(diphenylmethyl)azetidine

To a suspension of 8.6 g (0.22 mole) of sodium amide in 100 mL of dry toluene was added 18.8 g (0.2 mole) of phenol in 50 mL of dry toluene. The mixture was stirred at 60° C. for 2 hr. and the reaction temperature raised to 80° C. A solution of 63.4 g (0.2 mole) of 1-benzhydryl-3-methanesulfonyloxyazetidine (J. Org. Chem. 37, 3954 (1972)) in 200 ml of dry toluene was added dropwise. After stirring 2 hr at 80° C. the mixture was cooled and water added. The toluene was extracted with dilute NaOH solution, dried (Na$_2$SO$_4$) and concentrated. About one-third of the residue was removed. The rest of the residue was crystallized twice from water-isopropyl alcohol. Yield 9.3 g (15%); m.p. 83°-85° C.

Analysis: Calculated for C$_{22}$H$_{21}$NO: C, 83.78; H, 6.71; N, 4.44. Found: C, 83.69; H, 6.81; N, 4.41.

PREPARATION 3

1-(Diphenylmethyl)-3-azetidinecarbonitrile

Potassium cyanide (20.76 g, 318.9 mmol) and 1,4,7,10,13,16-hexaoxacyclooctadecane (18-Crown-6) (1.00 g, 3.78 mmol) were added to a stirring solution of 1-(diphenylmethyl)-3-azetidinol methanesulfonate ester (33.7 g, 106.3 mmol) in a methanol (200 mL): acetonitrile (100 mL) mixture. The reaction was stirred for 5 days. The reaction mixture was filtered and concentrated in vacuo. The residue was partitioned between 150 ml of 20% aqueous potassium carbonate and 150 mL ether. The layers were separated and the aqueous layer was extracted with 100 mL of ether. The organic solutions were combined and the filtrant was dissolved in the aqueous layer. This aqueous layer was extracted with ether (2×100 mL). These ethereal extracts were combined with the pooled organic extracts. This solution was dried (MgSO$_4$) and concentrated in vacuo. The residue was chromatographed (flash, silica gel, 2:8 ethyl acetate/hexane) to give 14.9 g (57%) as a white solid, mp 151°-152.5° C.

Analysis: Calculated for C$_{17}$H$_{16}$N$_2$: C, 82.23; H, 6.49; N, 11.28. Found: C, 82.17; H, 6.42; N, 11.21.

PREPARATION 4

1-(Diphenylmethyl)-3-azetididinecarboxylic acid methyl ester

A stirred slurry of 126.7 g (0.51 mole) of 1-diphenylmethyl-3-azetidinecarbonitrile in 1600 mL of 10% hydrogen chloride in methanol was heated until a clear solution, was obtained; then stirred for 16 h without further heating. The reaction mixture was concentrated in vacuo, and the residue partitioned between 1 L of ethyl ether and 500 mL of 10% sodium bicarbonate. The ether layer was removed, and the bicarbonate solution extracted with ethyl ether (2×200 mL). The combined ether layers were washed with 200 mL of brine solution, then concentrated in vacuo to give 140.9 g of crude product. The crude product was placed on a 1400 g silica gel column and eluted with 10% ethyl acetate/-methylene chloride. The forerun was discarded and the product collected in the next three 500 mL fractions, which when combined and concentrated yielded 84.4 g (59.2%) of product as an oil. The oil solidified on standing, and a sample was recrystallized for analysis from ligroin, mp 63°-65° C.

Analysis: Calculated for C$_{18}$H$_{19}$NO$_2$: C, 76.84; H, 6.81; N, 4.98. Found: C, 76.76; H, 6.83; N, 5.14.

PREPARATION 5

1-(Diphenylmethyl)-3-azetidinemethanol

A slurry of lithium aluminum hydride was formed by adding 6.83 g (0.18 mole) of lithium aluminum hydride in small portions to 150 mL of anhydrous tetrahydrofuran slowly stirred under nitrogen. The slurry was cooled to 0° C. in an ice bath and was treated with 84.4 g (0.3 mole) of 1-dimethylphenyl-3-azetidinecarboxylic acid methyl ester in 160 mL of anhydrous tetrahydrofuran added dropwise at a rate that allowed a steady evolution of gas and maintained the temperature below 5° C. After the addition, the reaction was stirred for 16 h then heated at reflux for 1 hr. Upon cooling the reaction mixture was treated by the careful addition of 35 mL of 3N sodium hydroxide. The solid precipitate was removed by filtration and the tetrahydrofuran filtrate concentrated in vacuo, 72.7 g. The residue was taken up in methylene chloride at which time a solid precipitated, which was collected by filtration, 40.6 g. The methylene chloride solution was washed with water, dried over magnesium sulfate, filtered, and concentrated in vacuo to obtain 25.7 g of residual oil. The yellow residue crystallized on standing. Proton nmr analysis showed both fractions (66.3 g, 87.2%) to be the expected product. A sample was recrystallized from ligroin, mp 114.5°-116° C. for analysis.

Analysis: Calculated for C$_{17}$H$_{19}$NO: C, 80.60; H, 7.56; N, 5.53. Found: C, 80.74; H, 7.59; N, 5.58.

PREPARATION 6

3-(2,6-Dimethylphenoxy)-1-(diphenylmethyl)azetidine

Methanesulfonyl chloride (14.3 g, 125 mmol) was slowly added to a solution of N-diphenylmethyl azetidin-3-ol (20.0 g, 83.7 mmol) and triethylamine (15.2 g, 151 mmol) in methylene chloride (160 mL) which was maintained at 0° C. by an ice-water bath. After 1.5 hours the slurry was diluted with methylene chloride (160 mL) and ice-water (160 mL). The layers were separated and the organic layer was washed with an ice-water mixture (160 mL), dried (MgSO$_4$), and concentrated in vacuo. A solution of the crude mesylate in dimethylformamide (100 mL) was added dropwise to a slurry of the sodium salt of 2,6-dimethylphenol in dimethylformamide prepared by adding a solution of 2,6-dimethylphenol (15.0 g, 125 mmol) in dimethylformamide to a slurry of sodium hydride (60% oil dispersion, 7.20 g, 150 mmol) which had been washed (3×60 mL) with hexane and diluted with dimethylformamide (130 mL). The reaction mixture was warmed at 50° for 42 h, cooled to room temperature and added to 1400 mL of an ice-water mixture. The aqueous slurry was extracted with ethyl acetate (3×200 mL). The combined organic extracts were washed with water (100 mL), saturated aqueous sodium chloride (100 mL), dried (MgSO$_4$) and concentrated in vacuo. The residue was chromatographed (silica gel, flash chromatography) eluting with ether/hexane (1:9) to give 15.0 g (52%) of white solid with a melting point of 99°-100° C.

Analysis: Calculated for C$_{24}$H$_{25}$NO: C, 83.93; H, 7.34; N, 4.08. Found: C, 83.92; H, 7.33; N, 4.09.

PREPARATION 7

3-Azetidinol (Z) 2-butenedioate (1:1)

A solution of 1-(diphenylmethyl)-3-azetidinol (20.0 g, 83.6 mmol) in absolute ethanol was hydrogenated on a Parr apparatus at 38° C. (initial pressure 50 psi) for 16 h after catalyst (10% Pd/C, 1 g) had been added. The slurry was cooled to ambient temperature, filtered through a pad of Celite, and concentrated in vacuo. Trituration of the residue with methylene chloride (50 mL) afforded 5.5 g (90%) of a white solid (in other runs trituration with hexane proved superior to methylene chloride). A 0.12 g sample was dissolved in ethanol and treated with maleic acid in ethanol. Diethyl ether was added and the white solid which formed was collected by filtration, mp 120°-121° C.

Analysis: Calculated for C$_3$H$_7$NO•C$_4$H$_4$O$_4$: C, 44.45; H, 5.86; N, 7.40. Found: C, 44.43; H, 5.96; N, 7.43.

PREPARATION 8

1-Acetyl-3-azetidinol

Acetyl chloride (923.1 g, 296 mmol) was added slowly to a stirring slurry of azetidin-3-ol (18.0 g, 246 mmol) and triethylamine (37.3 g, 369 mmol) in tetrahydrofuran (500 mL) maintained at −78° C. The reaction was allowed to warm slowly to ambient temperature over 2 h. The reaction mixture was filtered to remove some solid material and the solid was washed with tetrahydrofuran (~200 mL). The filtrate was concentrated in vacuo. The residue was diluted with hexane and concentrated (repeated twice) to give 23.2 g (82%) of a white solid. A small sample (0.5 g) was recrystallized from ethyl acetate and hexane to give 0.48 g of white solid, mp 57°-60° C.

Analysis: Calculated for C$_5$H$_9$NO$_2$: C, 52.16; H, 7.88; N, 12.17. Found: C, 52.01; H, 7.94; N, 12.17.

PREPARATION 9

1-Ethyl-3-azetidinol ethanedioate (1:1)

A solution of 1-acetyl-3-azetidinol acetate ester (3.9 g, 25 mmol) in tetrahydrofuran (20 mL) was added dropwise to a stirring slurry of lithium aluminum hydride (1.9 g, 50 mmol) in tetrahydrofuran maintained at −20° C. After 30 min the reaction mixture was quenched by the sequential addition of 20 mL of 10% aqueous tetrahydrofuran, 2.9 mL of 10% aqueous sodium hydroxide, and 6 mL of $H_2O$. After a granular white solid formed, the reaction mixture was filtered through a pad of Celite, dried ($MgSO_4$), and concentrated in vacuo to give 1.4 g (45%) of the free base as a brown oil. The free base was dissolved in ethanol and treated with a solution of oxalic acid in ethanol. The solid which formed was collected by filtration, mp 77.5°–79° C.

Analysis: Calculated for $C_5H_{11}NO \cdot C_2H_2O_4$: C, 43.98; H, 6.85; N, 7.33. Found: C, 43.94; H, 7.00; N, 7.24.

PREPARATION 10

1-(1-Phenylethyl)-3-azetidinol(Z)-2-butenedioate

A solution of 60.59 g (0.5 mole) of α-phenethylamine and 46.27 g (0.5 mole) of epichlorohydrin in 200 mL of methanol was allowed to stand protected from light for 96 hours. The reaction was then stirred at reflux for 72 hours and the solvent was removed in vacuo. Trituration of the oil residue with isopropyl ether gave some white crystalline product (α-phenethylamine hydrochloride) which was removed by filtration. The crude product solution was converted to the free base by adding ammonium hydroxide and extracting with 4×200 mL of toluene. The toluene extracts were combined, dried over $MgSO_4$ and filtered. The filtrate was treated with 58 g of maleic acid dissolved in 800 mL of methylisobutyl ketone. The crude maleate salt was collected to yield 62 g (42.4%). A sample was recrystallized from ethyl acetate for elemental analysis, mp 113°–114° C.

Analysis: Calc. for $C_{11}H_{15}NO \cdot C_4H_4O_4$: C, 61.42; H, 6.53; N, 4.78. Found: C, 61.37; H, 6.65; N, 4.80.

PREPARATION 11

1-Acetyl-3-(2,6-dimethylphenoxy)azetidine

Triethylamine (10.8 g, 106 mmol) was added to a stirred slurry of 3-(2,6-dimethylphenoxy)azetidine monohydrochloride (9.10 g, 42.7 mmol) in tetrahydrofuran (500 mL). After 10 minutes the reaction mixture was cooled to 0° C., and a solution of acetyl chloride (5.03 g, 64.1 mmol) in 50 mL of tetrahydrofuran was added dropwise. The reaction mixture was allowed to come to ambient temperature and was stirred overnight. The reaction mixture was then filtered and the filtrate concentrated in vacuo. The residue was chromatographed (flash, $SiO_2$) eluting with methylene chloride/methanol (9:1) to give 9.00 g (99%) of yellow powder with a melting point of 40.0°–42.5° C.

Analysis: Calculated for $C_{13}H_{17}NO_2$: C, 71.21; H, 7.81; N, 6.39. Found: C, 70.86; H, 7.85; N, 6.32.

PREPARATION 12

1,3-dichloro-2-diphenylmethoxypropane

A stirred solution of 508 g (2.5 mol) of diphenylmethylchloride and 387 g (3 mol) of 1,3-dichloro-2-propanol in 700 mL of dry toluene was heated at reflux temperature for 72 hr. The reaction mixture was concentrated in vacuo and the residual oil distilled to give 587 g (80%) of colorless oil; bp 137°–140° C./0.1 mm.

Analysis: Calculated for $C_{16}H_{16}Cl_2O$: C, 65.09; H, 5.46. Found: C, 65.36; H, 5.40.

PREPARATION 13

3-Diphenylmethoxy-1-methylazetidine

A solution of 244. g (0.83 mole) of 1,3-dichloro-2-diphenylmethoxypropane in 300 ml of methylamine was heated in a steel bomb to 100° for 18 hours. The mixture was concentrated, and the residue partitioned between chloroform and dilute hydrochloric acid. The acid solution was washed twice with chloroform, and the chloroform solutions combined. The chloroform was extracted with dilute sodium hydroxide, dried with sodium sulfate, and concentrated. The residue was distilled (b.p. 125°–130°/0.1 mm) to yield 104 g (40%). The distillate crystallizes on standing and can be recrystallized from isooctane, mp 44°–48°.

Analysis: Calculated for $C_{17}H_{19}NO$: C, 80.59; H, 7.56; N, 5.53. Found: C, 80.47; H, 7.50; N, 5.43.

PREPARATION 14

1-Ethyl-3-diphenylmethoxyazetidine

Following the procedure of Preparation 13, the title compound was prepared from 1,3-dichloro-2-diphenylmethoxypropane (44.0 g, 0.15 mol) and ethylamine (100 ml) in 47.5% yield; bp 135°–142° C./0.10 mm.

PREPARATION 15

1-Methyl-3-azetidinol hydrochloride

A. A solution of 70 g (0.288 mole) of 1-methyl-3-diphenylmethoxyazetidine in 200 ml of absolute ethanol was shaken with about 4 g of 10% Pd/C in three atmospheres of hydrogen at about 60° C. for three hours. The mixture was filtered and the filtrate made acidic with hydrogen chloride gas while cooling in an ice bath. The acidic solution was concentrated at reduced pressure and the solid residue was triturated twice with ether and the ether decanted. The solid residue was dissolved in 200 ml absolute ethanol, 100 ml of ether was added and the solution placed in the freezer (−14° C.). The crystalline solid which separated was collected and dried, giving 27 g (75%) of 1-methyl-3-azetidinol hydrochloride melting at 87°–95° C. A sample recrystallized from an absolute ethanol-ether mixture melted at 93°–95° C.

PREPARATION 16

1-Ethyl-3-azetidinol

1-Ethyl-3-azetidinol was prepared from 1-ethyl-3-diphenylmethoxyazetidine by hydrogenolysis using the procedure described in Example 6. The proton nuclear magnetic resonance spectrum was consistent with the proposed structure.

PREPARATION 17

1-(1-Phenylethyl)-3-azetidinol methansulfonate ester

Methanesulfonyl chloride (3.42 g, 0.030 mol) was added dropwise to a stirred solution of 1-(1-phenylethyl)-3-azetidinol (3.54 g, 0.020 mol) and triethylamine (3.84 g, 0.036 mole) in methylene chloride (35 ml) maintained at 0° C. After the addition was complete, the reaction mixture was stirred for 20 minutes at 0° C. and then added to 25 ml of a water/ice mixture. The methylene chloride layer was washed (H₂O), dried (MgSO₄) and concentrated in vacuo to obtain the title compound.

PREPARATION 18

1-(1-Phenylethyl)-3-azetidinecarbonitrile (Z)-2-butenedioate (1:1)

A slurry of methanesulfonate ester of 1-(1-phenylethyl)azetidin-3-ol (60.4 g, 223 mmol), potassium cyanide (43.5 g, 669 mmol) and methanol (350 mol) were allowed to stir at ambient temperature for 72 h. The reaction mixture was filtered and the filtrate was concentrated in vacuo. The residue was partitioned between 300 mL of an aqueous 20% potassium carbonate solution and 400 mL of diethyl ether. The organic layer was separated, dried (MgSO₄) and concentrated in vacuo. The residue was chromatographed (SiO₂, flash, ethyl acetate/hexane 1:3) to give 25.1 g (56%). A 1-g portion was dissolved in 2-propanol and treated with maleic acid (0.75 g, 6.5 mmol). The resulting solid was recrystallized from 2-propanol to give a white solid, mp 147°–148° C.

Analysis: Calculted for $C_{12}H_{14}N_2 \cdot C_4H_4O_4$: C, 63.56; H, 6.00; N, 9.23. Found: C, 63.36; H, 5.97; N, 9.18.

PREPARATION 19

1-(1-Phenylethyl)-3-azetidinecarboxylic acid methyl ester ethanedioate (1:1) hemihydrate A solution of 1-(1-phenylethyl)-3-azetidinecarbonitrile (41.5 g, 220 mmol) in 1 L of 10% methanolic HCl was allowed to stand, protected from the atmosphere by an N₂ bubbler, at ambient temperature for 48 h. The reaction mixture was concentrated in vacuo, and the residue was partitioned between 500 mL of ether and 500 mL of saturated aqueous sodium bicarbonate. The layers were separated, and the aqueous layer was extracted with ether (2 × 100 mL). The combined ethereal extracts were dried (Na₂SO₄) and concentrated in vacuo to give a brown oil. The oil was chromatographed (SiO₂, Flash, 1:3 ethyl acetate/hexane) to give 43.3 g (90%) of product. A 1-g sample was dissolved in ethanol and was added to 0.6 of oxalic acid in ethanol. The solid which formed was collected by filtration. Recrystallization from ethanol-ether afforded a white solid; mp 95°–96.5° C.

Analysis: Calc. for $C_{15}H_{12}NO_2 \cdot 0.5H_2O$: C, 56.598; H, 46.333; N, 4.40. Found: C,56.51; H, 6.00; N, 4.31.

PREPARATION 20

1-(1-Phenylethyl)-3-azetidinemethanol

Following the procedures of Preparation 5, the title compound was prepared from 1-(1-phenylethyl)-3-azetidinecarboxylic acid methyl ester.

PREPARATION 21

1-(1-Phenylethyl)-3-azetidinemethanol methanesulfonate ester

The title compound is prepared from 1-(1-phenylethyl)-3-azetidinemethanol following the procedures of preparation 1.

PREPARATION 22

1-(1-Phenylethyl)-3-azetidineacetonitrile

Following the procedures of Preparation 3, the title compound is prepared from 1-(1-phenylethyl)-3-azetidinemethanol methanesulfonate ester.

PREPARATION 23

1-(1-Phenylethyl-3-azetidineacetic acid methyl ester

Following the procedures of Preparation 4, the title compound is prepared from 1-(1-phenylethyl)-3-azetidineacetonitrile.

PREPARATION 24

1-(1-phenylethyl)-3-azetidineethanol

The title compound is prepared from 1-(1-phenylethyl)-3-azetidineacetic acid methyl ester according to the procedures of preparation 5.

PREPARATION 25

1-(1-Phenylethyl)-3-azetidineethanol methanesulfonate ester

The methanesulfonate ester is prepared from 1-(1-phenylethyl)-3-azetidineethanol following the procedures of preparation 1.

PREPARATION 26

1-(1-Phenylethyl)-3-azetidinepropionitrile

The title compound is prepared from 1-(1-phenylethyl)-3-azetidineethanol methanesulfonate ester according to the procedures of preparation 3.

PREPARATION 27

1-(1-Phenylethyl)-3-azetidinepropionic acid methyl ester

The title compound is prepared from 1-(1-phenylethyl)-3-azetidinepropionitrile following the hydrolysis procedures of preparation 4.

PREPARATION 28

1-(1-Phenylethyl)-3-azetidinepropanol

The title compound is prepared from 1-(1-phenylethyl)-3-azetidinepropionic acid methylester following the reduction procedures of preparation 5.

PREPARATION 29

1-(1-Phenylethyl)-2-azetidineethanol

Following the procedures used in preparations 21 through 24, the title compound is prepared from 1-(1-phenylethyl)-2-azetidinemethanol.

PREPARATION 30

1-(1-phenylethyl)-2-azetidinepropanol

The title compound is prepared from 1-(1-phenylethyl)-2-azetidineethanol repeating the procedures used in preparation 29.

EXAMPLE 1

2-(Phenoxymethyl)-1-(phenylmethyl)azetidine ethanedioate hydrate (2:2:1)

Acetonitrile (50 mL), triphenyl phosphine (2.07 g, 7.91 mmol), and carbon tetrachloride (2.20 g, 14.4 mmol) were added to a flask containing 1-benzyl-3-hydroxy-4-phenoxybutylamine (1.95 g, 7.19 mmol). After solution was effected, triethylamine (0.80 g, 7.91 mmol) was added, and the reaction was allowed to stir at ambient temperature for 16 h. The reaction mixture was concentrated in vacuo and partitioned between 20 mL of saturated aqueous sodium bicarbonate and 20 mL methylene chloride. The layers were separated, and the aqueous layer was extracted (2×30 mL) with methylene chloride. The combined organic extracts were washed with water (20 mL), dried (MgSO$_4$), and concentrated in vacuo. The residue was chromatographed (flash, silica gel, 1:1 ether/hexane) to give 0.95 g (52%) of clear oil. The oil was dissolved in ethyl acetate and added to a solution of oxalic acid in ethyl acetate. The white solid which formed was collected by filtration, mp 104°–108° C.

Analysis: Calc. for C$_{17}$H$_{19}$NO•C$_2$H$_2$O$_4$•0.5H$_2$O: C, 64.761; H, 6.293; N, 3.975. Found: C, 64.50; H, 6.03; N, 3.91.

EXAMPLE 2

3-[(2,6-Dimethylphenoxy)methyl]-1-ethylazetidine monohydrochloride

A solution of acetyl chloride (3.17 g, 40.4 mmol) in tetrahydrofuran (20 mL) was added dropwise to a stirring solution of 3-[(2,6-dimethylphenoxy)methyl]azetidine (6.45 g, 33.7 mmol) and triethylamine (5.10 g, 50.5 mmol) in tetrahydrofuran (150 mL) maintained at −20° C. After 1 h the reaction mixture was warmed to 0° C. over 1 h. The reaction slurry was filtered through a pad of Celite and concentrated in vacuo to give 8.0 g of the crude amide.

A solution of the crude acetamide (8.0 g, ~34 mmol) in tetrahydrofuran (50 mL) was added dropwise to a stirring slurry of lithium aluminum hydride (1.43 g, 37.7 mmol) in tetrahydrofuran (125 mL) maintained at 0° C. After the addition was complete, the reaction was stirred for 30 min. at 0° C. Aqueous tetrahydrofuran (90% tetrahydrofuran, 15 mL), 10% aqueous sodium hydroxide (2.25 mL) and water (4.5 mL) were added sequentially, and the reaction mixture was stirred until a granular white solid formed. The reaction mixture was filtered through a pad of Celite. The filtrate was dried with magnesium sulfate, and concentrated in vacuo. The residue was chromatographed (silica gel, flash, 9:1 CH$_2$Cl$_2$/MeOH) to give 4.5 g (60%) of the product.

The oil was dissolved in ethanol, and ethereal HCl was added. The solid which formed was collected by filtration and was recrystallized from an ethanol-ether mixture to give a white solid, mp 138°–139° C.

Analysis: Calculated for C$_{14}$H$_{21}$NO•HCl: C, 65.74; H, 8.67; N, 5.48. Found: C, 65.54; H, 8.77; N, 5.48.

EXAMPLE 3

1-(1-Phenylethyl)-3-[[3-(trifluoromethyl)phenoxy]methyl]azetidine (Z)-2-butenedioate (1:1)

Methanesulfonyl chloride (9.5 g, 65 mmol) was added dropwise to a solution of 3-(hydroxymethyl)-1-(1-phenethyl)azetidine (8.3 g, 43 mmol) and triethylamine (8.0 g, 79 mmol) in methylene chloride (50 mL) maintained at 0° C. After the addition was complete, the mixture was stirred for 0.5 h. The reaction mixture was added to 200 mL of an ice-water solution. The layers were separated, and the aqueous layer was extracted with methylene chloride (50 mL). The combined organic extracts were washed with water, dried (MgSO$_4$), and concentrated in vacuo. The residue was dissolved in dimethylformamide (50 mL), and the resulting solution was added dropwise to a stirring slurry of the sodium salt of 3-trifluoromethylphenol which was prepared by adding a solution of 3-(trifluoromethyl)phenol (10.6 g, 65.2 mmol) in dimethylformamide (25 mL) to a slurry of sodium hydride [sodium hydride 60% oil dispersion (4.7 g, 98 mmol) washed (3×30 mL) with hexane] in dimethylformamide (125 mL). After the crude mesylate was added, the reaction mixture was allowed to stir at ambient temperature for 15 h.

The reaction mixture was added to 1 L of water, and the resulting solution was extracted (2×200 mL) with ethyl acetate. The combined organic extracts were washed with water (200 mL) and saturated aqueous sodium chloride. The resulting organic solution was dried (MgSO$_4$) and concentrated in vacuo to give a brown residue. The residue was chromatographed (SiO$_2$, flash, ethyl acetate-hexane 1:1) to give 4.0 g (27.5%) of the product. A small sample of the product (200 mg) in 2-propanol was added to 83 mg of maleic acid in 2-propanol. Isopropylether was added and a solid precipitated. The solid was collected by filtration and was recrystallized from ethanol-ether to give a white solid, mp 102°–103° C.

Analysis: Calc. for C$_{19}$H$_{20}$NOF$_3$•C$_4$H$_4$O$_4$: C, 61.19; H, 5.36; N, 3.10. Found: C, 60.93; H, 5.38; N, 3.12.

EXAMPLE 4

1-Methyl-3-phenoxyazetidine maleate

To a solution of 3 g (0.084 mole) of NaNH$_2$ in 250 ml of DMSO was added dropwise with stirring and ice bath cooling 7.9 g (0.077 mole) of phenol in DMSO at 25°–30° C. An aqueous solution of 10 g (0.07 mole) of 3-chloro-1-methylazetidine hydrochloride was made basic with NaOH and extracted with isopropyl ether. The ether solution was dried by passing through a column of type 4A molecular sieves. This solution was added to the above prepared sodium phenolate solution and the mixture heated to 130° C. for 18 hours. The mixture was diluted with an equal volume of H$_2$O, a little dilute NaOH added and extracted with isopropyl ether. The ether layer was dried and concentrated. The fumarate salt was prepared on the residue in isopropyl alcohol-isopropyl ether and recrystallized from the same solvent. Yield, 3.2 g (16.5%); mp 87°–98° C. The material has an impurity as seen on the NMR but further recrystallization enriches the sample in the impurity.

Analysis: Calculated for C$_{14}$H$_{17}$NO$_5$: C, 60.21; H, 6.14; N, 5.02. Found: C, 59.16; H, 6.02; N, 4.86.

EXAMPLE 5

3-[3-(Trifluoromethyl)phenoxy]-1-[1-phenylethyl]azetidine ethanedioate (1:1)

The maleate of 1-[1-phenylethyl]-3-hydroxyazetidine weighing 71.5 g (0.244 mole) was partitioned between toluene and a dilute sodium hydroxide solution. The toluene layer was dried (MgSO$_4$), filtered and concentrated in vacuo. The residue was dissolved in 100 ml dry dimethylformamide and was added dropwise to 13.8 g (0.29 mole) of 50% sodium hydride (in mineral oil) suspended in 400 ml of dry dimethylformamide at 70° C. The temperature and stirring were maintained for 1 hr; then 40 g (0.244 mole) of 3-trifluoromethyl fluorobenzene was added, and the mixture brought to reflux for 5 hr. An equal volume of water was added, and the mixture was made acidic by adding dilute hydrochloric acid and washed with 300 ml isopropyl ether. The aqueous acidic layer was then basified by adding dilute sodium hydroxide solution and extracted with isopropyl ether. This isopropyl ether layer was dried, filtered, and concentrated in vacuo. The residue was dissolved in isopropyl alcohol and treated with 15 g of oxalic acid.

The resulting salt was recrystallized from isopropyl alcohol to yield 76 g (75%); mp 150°-153° C.

Analysis: Calculated for $C_{20}H_{20}F_3NO_5$: C, 58.39; H, 4.90; N, 3.41. Found: C, 58.41; H, 4.93; N, 3.41.

EXAMPLE 6

3-[3-(Trifluoromethyl)phenoxy]azetidine N-cyclohexylsulfamate (1:1)

Forty grams (0.097 mole) of 3-[3-(trifluoromethyl)-phenoxy]-1-[1-phenylethyl]azetidine ethanedioate was partitioned between a dilute sodium hydroxide solution and chloroform. The chloroform solution was dried, filtered and concentrated in vacuo. The residue was dissolved in 300 ml of methanol, treated with 1.0 g of 20% $Pd(OH)_2/C$, and the mixture hydrogenated in a large Parr apparatus for 5 hours at 80°. After cooling and filtering, the filtrate was concentrated in vacuo, and the residue was treated with 10.0 g of oxalic acid dissolved in 100 ml of isopropyl alcohol. The resulting salt weighed 20 g; mp 142°-145°. The nmr, tlc and mass spectrum indicated the product was a mixture of the desired product and an impurity. The salt was partitioned between chloroform and dilute NaOH. The chloroform solution was dried ($Na_2SO_4$) and concentrated. The residue was treated with cyclohexyl sulfamic acid in isopropyl alcohol and the resultant crystals were recrystallized form the same solvent to yield 14.0 g (35%); mp 123°-125°.

Analysis: Calculated for $C_{16}H_{23}F_3N_2O_4S$: C, 48.48; H, 5.85; N, 7.07. Found: C, 48.08; H, 5.94; N, 6.97.

EXAMPLE 7

3-Phenoxyazetidine methylsulfonate

A 200 ml solution of 7.8 g (0.025 mole) of 3-phenoxy-1-(diphenylmethyl)azetidine in ethanol was treated with $Pd(OH)_2$ (20% Pd) and hydrogenated at about 45 psi and 80° C. for 23 hr. The mixture was filtered and the filtrate concentrated. The residue was diluted to 30 ml with ethanol and 2.5 g of methanesulfonic acid added. The resulting crystals were recrystallized from ethanol, yielding 2.3 g (37.5%); mp 128°-130° C.

Analysis: Calculated for $C_{20}H_{15}NO_4S$: C, 48.97; H, 6.16; N, 5.71. Found: C, 48.40; H, 6.19; N, 5.63.

EXAMPLE 8

3-[(2,6-Dimethylphenoxy)methyl]-1-(1-phenylethyl)azetidine ethanedioate (1:1)

Methanesulfonyl chloride (13.9 g, 121 mmol) was added dropwise to a stirring solution of 3-(hydroxymethyl)-1-(1-phenylethyl)azetidine (15.5 g, 81.1 mmol) and triethylamine (14.8 g, 146, 146 mmol) in methylene chloride (300 mL) which was cooled in a ice/water bath. After 1.5 h the slurry was added to 250 mL of an ice-water mixture. The layers were allowed to separate, and the organic layer was washed with water (200 mL), dried ($MgSO_4$) and concentrated in vacuo. A solution of the crude mesylate in dimethylformamide (100 mL) was added dropwise to a slurry of the sodium salt of 2,6-dimethylphenol in dimethylformamide at 0° C. [The sodium salt of 2,6-dimethylphenol was formed by adding a solution of 2,6-dimethylphenol (14.8 g, 122 mmol) in dimethylformamide (60 ml) to a slurry of sodium hydride (60% oil dispersion 7.00 g, 146 mmol) which had been washed (3×60 ml) with hexane]. The reaction mixture was stirred 18 h at ambient temperature and then added to 1 liter of a water-ice mixture. The resulting slurry was extracted with ethyl acetate (2×200 mL). The combined organics were washed with water (200 mL) and brine (200 mL), dried ($MgSO_4$), and concentrated in vacuo. The residue was chromatographed ($SiO_2$, flash, 25% ethyl acetate-hexane) to afford 17.1 g (64%) of product. A 1-g sample was dissolved in ethyl acetate and added to a solution of oxalic acid in ethyl acetate. The solid which formed was collected by filtration and recrystallized from ethyl acetate to give a white solid, mp 137°-138° C.

Analysis: Calculated for $C_{20}H_{25}NO \cdot C_2H_2O_4$: C, 68.55; H, 7.06; N, 3.63. Found: C, 68.39; H, 7.13; N, 3.63.

EXAMPLE 9

3-[(2,6-Dimethylphenoxy)methyl]azetidine (Z)-2-butendioate (1:1)

Triethylamine (2 mL) was added to a solution of 3-[(2,6-dimethylphenoxy)methyl]-1-(1-phenylethyl)azetidine (6.01 g, 21.3 mmol) in absolute ethanol (100 mL). The solution was hydrogenated on a Parr apparatus with approximately 1 g of 10% Pd on carbon as a catalyst at 55° C. and 60 psi (initial pressure) overnight. The mixture was cooled, filtered, and concentrated in vacuo. The residue was dissolved in 2-propanol and added to a solution of maleic acid (2.1 g, 18 mmol). The solid which formed was collected by filtration and recrystallized from 2-propanol to give 5.3 g (81%) of white solid; mp 150°-151.5° C.

Analysis: Calculated for $C_{12}H_{17}NO \cdot C_4H_4O_4$: C, 62.53; H, 6.89; N, 4.57. Found: C, 62.44; H, 6.98; N, 4.53.

EXAMPLE 10

3-(2,6-dimethylphenoxy)azetidine monohydrochloride

A solution of 3-(2,6-dimethylphenoxy)-1-(diphenylmethyl)azetidine (13.9 g, 40.4 mol) and triethylamine (3 mL) in absolute ethanol (120 mL) was hydrogenated on a Parr apparatus with 1.5 g of 10% palladium on charcoal catalyst at 60 psi at 60° C. for 16 h. After the calculated amount of hydrogen had been absorbed, the catalyst was removed by filtration through a pad of Celite, and the filtrate was concentrated in vacuo. The residue was dissolved in methanol and treated with ethereal HCl. The resulting salt was recrystallized from methanol-diethyl ether to give 5.5 g (64%) of a white crystalline solid, mp 165.5°-167.5° C.

Analysis: Calculated for $C_{11}H_{15}NO \cdot HCl$: C, 61.82; H, 7.55; N, 6.55. Found: C, 61.74; H, 7.64; N, 6.58.

EXAMPLE 11

1-Ethyl-3-(2,6-dimethylphenoxy)azetidine monohydrochloride

A solution of 1-acetyl-3-(2,6-dimethylphenoxy)azetidine (9.00 g, 41 mmol) in tetrahydrofuran (125 mL) was added to a slurry of lithium aluminum hydride (3.1 g, 82 mmol) maintained at 0° C. After the addition was complete (~1 h), the reaction was quenched by the sequential addition of 30 mL 10% water in tetrahydrofuran, 3 mL of 15% sodium hydroxide in water and 9 mL of water. The slurry was stirred for 20 minutes, filtered and concentrated in vacuo. The residue was chromatographed (200 g, $SiO_2$, 9:1 $CH_2Cl_2$:MeOH) to give the amine, which was dissolved in ethanol and treated with ethereal HCl. The solid which formed was recrystallized from ethanoldiethyl ether to give 4.2 g (50%) of white solid, mp 142°-143.5° C.

Analysis: Calculated for $C_{13}H_{19}NO \cdot HCl$: C, 64.59; H, 8.34; N, 5.79. Found: C, 64.55; H, 8.38; N, 5.82.

EXAMPLE 12

3-[2-(4-Nitrophenoxy)ethyl]-1-(1-phenylethyl)azetidine

The title compound is prepared according to the procedures of Example 3 from 1-(1-phenylethyl)-3-azetidine ethanol and 4-nitrophenol.

EXAMPLE 13

3-[2-(4-Aminophenoxy)ethyl]-1-(1-phenylethyl)azetidine

The title compound is prepared by catalytic reduction at room temperature in the presence of platinum on carbon catalyst in ethanol solution using standard laboratory procedures from 3-[2-(4-nitrophenoxy)ethyl]-1-(1-phenylethyl)azetidine.

EXAMPLE 14

N-Methyl-N'-[4-[2-[1-(1-phenylethyl)-3-azetidinyl]ethoxy]phenyl]urea

Under anhydous conditions, methyl isocyanate (10 mmol) is added dropwise to a stirred solution of 3-[2-(4-aminophenoxy)ethyl]-1-(1-phenylethyl)azetidine (10 mmol) in chloroform (100 ml). After stirring for 3 hr the solvent is removed and the residue purified by standard laboratory procedures.

EXAMPLE 15

2-[(3-Chlorophenoxy)propyl]-1-(1-phenylethyl)azetidine

The title compound is prepared from 1-(1-phenylethyl)-2-azetidine propanol methanesulfonate ester and 3-chlorophenol following the procedures of Example 8.

EXAMPLE 16

1-Methyl-3-(4-methoxphenoxy)azetidine

The title compound is prepared from 1-methyl-3-azetidinol and 4-methoxyphenol following the procedures of Example 8.

EXAMPLE 17

1-(1,1-dimethylethyl)-3-[(4-methylphenoxy)methyl]azetidine

Following the procedures of Example 8, the title compound is prepared from 1-t-butyl-3-azetidinemethanol and p-cresol.

EXAMPLE 18

1-(1-methylethyl)-2-[4-(phenoxy)phenoxymethyl]azetidine

The title compound is prepared from 1-(1-methylethyl)-2-azetidinemethanol and 4-phenoxyphenol according to the procedures of Example 8.

EXAMPLE 19

1-Ethyl-3-(4-nitrophenoxy)azetidine

The title compound is prepared from 1-ethyl-3-azetidinol and 1-fluoro-4-nitrobenzene according to the procedures of Example 5.

EXAMPLE 20

3-(4-Aminophenoxy)-1-ethylazetidine

A solution of 1-ethyl-3-(4-nitrophenoxy)azetidine in ethanol is subjected to catalytic reduction using palladium on carbon catalyst using standard procedures to obtain the title compound.

EXAMPLE 21

1-Ethyl-3-[(4-methanesulfonylamino)phenoxy]azetidine

A solution of methanesulfonyl chloride (10 mmol) in methylene chloride is added dropwise to a cold (0° C.) stirred solution of 3-(4-aminophenoxy)-1-ethylazetidine (10 mmol) and triethylamine (15 mmol) in methylene chloride. After stirring for 30 min the reaction mixture is stirred at ambient temperature overnight. The reaction mixture is washed successively with 1N sodium hydroxide solution and water, dried, and concentrated to obtain the product which is purified by conventional techniques.

TABLE I $$Ar-O-(CH_2)_n \begin{array}{c} 3 \\ \boxed{\phantom{X}} \\ 2 \end{array} N-R$$

| Example | Ar | n | position | R |
|---|---|---|---|---|
| 1 | $C_6H_5$ | 1 | 2 | $-CH_2C_6H_5$ |
| 2 | $2,6\text{-diMeC}_6H_3-$ | 1 | 3 | Et |
| 3 | $3\text{-CF}_3C_6H_4$ | 1 | 3 | $-CH(CH_3)C_6H_5$ |
| 4 | $C_6H_5$ | 0 | 3 | Me |
| 5 | $3\text{-CF}_3C_6H_4$ | 0 | 3 | $-CH(CH_3)C_6H_5$ |
| 6 | $3\text{-CF}_3C_6H_4$ | 0 | 3 | H |
| 7 | $C_6H_5$ | 0 | 3 | H |
| 8 | $2,6\text{-diMeC}_6H_3-$ | 1 | 3 | $-CH(CH_3)C_6H_5$ |
| 9 | $2,6\text{-diMeC}_6H_3-$ | 1 | 3 | H |
| 10 | $2,6\text{-diMeC}_6H_3-$ | 0 | 3 | H |
| 11 | $2,6\text{-diMeC}_6H_3-$ | 0 | 3 | Et |
| 12 | $4\text{-NO}_2C_6H_4$ | 2 | 3 | $-CH(CH_3)C_6H_5$ |
| 13 | $4\text{-NH}_2C_6H_4$ | 2 | 3 | $-CH(CH_3)C_6H_5$ |
| 14 | $4\text{-CH}_3\text{NHCNHC}_6H_4$ (O, ‖) | 2 | 3 | $-CH(CH_3)C_6H_5$ |
| 15 | $3\text{-ClC}_6H_4$ | 3 | 2 | $-CH(CH_3)C_6H_5$ |
| 16 | $4\text{-CH}_3OC_6H_4$ | 0 | 3 | Me |
| 17 | $4\text{-CH}_3C_6H_5$ | 1 | 3 | -t-Butyl |
| 18 | $4\text{-C}_6H_5OC_6H_4-$ | 1 | 2 | -iPr |
| 19 | $4\text{-NO}_2C_6H_4-$ | 0 | 3 | Et |
| 20 | $4\text{-NH}_2C_6H_4$ | 0 | 3 | Et |
| 21 | $4\text{-CH}_3SO_2NHC_6H_4$ | 0 | 3 | Et |

PHARMACOLOGICAL METHODS

Coronary Artery Ligation Induced Arrhythmias

Adult mongrel dogs which are in the conscious state were used for the test and cardiac arrhythmias were induced by prior (22-24 hr) surgical preparation in which blood flow through a coronary artery was occluded by use of a constrictor device as reported by Smith et al. 1973. A Grass Model 79 Polygraph was used for recording the electrocardiogram (Grass 7P4 Preamplifier).

The test compound was administered by infusion (Harvard Model 942 Infusion Pump) into a saphenous vein to one group of dogs at a rate of 0.5 mg/kg/min. Concentration of compound was adjusted according to the weight of the dog to allow a volume of infusion of 0.5 ml/min. The test compound was administered orally by gavage to another group of dogs at dose levels of 10 through 40 mg/kg. The test compound was prepared in distilled water to give a total volume of 20 ml. Following the administration of the test compound, the heart rate, number of ectopic cardiac beats per min, and the percent ectopic beats (ectopic beats/HR × 100) were recorded at 15 min intervals. The compound was considered active if it abolished the ectopic ventricular frequency and caused a return to normal sinus rhythm within 2 hours of administration. The test results are summarized in Table II. Cardiac arrhythmias produced by modification of method of Harris, 1950, Circulation 1, 1318, as reported by Smith et al. 1973, Pharmacologist 15, 192.

TABLE II

| | Coronary Occlusion Antiarrhythmic Activity | |
|---|---|---|
| Ex. | No. Active/ No. Tested | MED$_{100}$*(mg/kg IV) |
| 2 | 1/2 | 4 |
| 9 | 4/4 | 10.5 |
| 10 | 1/4 | 20 |
| 11 | 2/4 | 9.5 |

*Minimum Effective Dose required to abolish all ectopic cardiac beats

Electrical Shock Induced Convulsions

Adult female mice in groups of eight were administered the test drug intraperitoneally (usually 100 mg/kg initially for screening) in liquid carrier, usually physiological saline or water. Animals were challenged electrically by placing brass electrodes on the corneas and applying an electrical stimulus (60 Hz, 5 m sec. pulse width, 34 m A intensity) for 0.2 seconds by way of a Grass Stimulator ® and constant current unit and a Hunter Timer ®. The absence of tonic seizures upon cessation of the stimuli was scored as protection in that animal. The number of animals protected from tonic seizures at a given dose of test drug was determined. The ED50, 95% confidence limits and potency ratio may be ascertained by the method of J. T. Litchfield and F. Wilcoxon (1949) J. PHARMACOL. EXP. THER. 96, 99-113. The compound of Example 11 had an ED$_{50}$ of 17.8 mg/kg (IP).

Pharmaceutical Compositions

This invention further provides pharmaceutical compositions for administration to a warm-blooded animals comprising at least one of the compounds according to the invention in association with a pharmaceutical carrier or excipient. The compounds are thus presented in a therapeutic composition suitable for oral, rectal, or parenteral administration, i.e., capsules, tablets, coated tablets or liquid for oral administration, suppositories for rectal administration, and sterile solutions or suspensions for administration by injection or intravenous administration.

For solid oral dosage forms, suitable carriers or excipients include lactose, potato and maize starches, talc, gelatin, stearic acid, silicic acid, magnesium stearate and polyvinylpyrrolidone. A suitable carrier for a liquid oral dosage form is purified water.

For parenteral administration, the carrier or excipient can be a sterile parenterally acceptable liquid, e.g., water or arachis oil, contained in ampoules.

In compositions for rectal administration the carrier can comprise a suppository base, e.g., cocoa butter or a glyceride.

Advantageously, the compositions are formulated as dosage units, each unit being adapted to supply a fixed dose of active ingredients. It is only necessary that the active ingredient constitute an effective amount such that a suitable effective dosage will be consistent with the dosage form employed and administered in multiple units if necessary. The exact individual dosages, as well as daily dosages, will of course, be determined according to standard medical principles under the direction of a physician or veterinarian. Generally, the following guide to projected human oral doses is derived by knowledge of the activity obtained in animal screening tests for the various indications in the methods of the invention compared to activity of known agents in the field in the same animal tests. However, the amount of the active compounds administered need not be limited by these comparisons due to uncertainty in transposing ocmparative animal data to human treatments.

Projected oral dosages for treating cardiac arrhythmias in humans are of the order of 10-1000 mg/kg/day given in divided dosages two to four times per day of from 5 to 250 mg/kg. The projected dosage for treating convulsions is from 2 to 180 mg/kg/day which may be given in divided doses of from 0.5 to 60 mg/kg two to four times each day. Obviously, with each indication, it may be necessary to adjust the unit dosage amount and frequency of administration to obtain the desired therapeutic effect.

Other routes of administration such as intramuscularly or intravenously are possible with dosage forms being adapted to the situation as will be obvious to one skilled in the art of medicine.

Various modifications and equivalents will be apparent to one skilled in the art and may be made in the compounds, methods of treatment and compositions of the present invention without departing from the spirit or scope thereof, and it is therefore to be understood that the invention is to be limited only the the scope of the appended claims.

What is claimed is:

1. A method of treating cardiac arrhythmias in warm-blooded animals which comprises administering thereto a therapeutically effective amount of a compound having the formula:

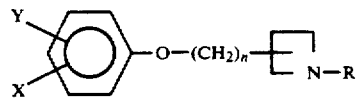

wherein n is 0 to 3, R is hydrogen, $C_1$-$C_4$ alkyl, or arylalkyl; X is selected from the group consisting of hydrogen, halogen, trifluoromethyl, $C_1$-$C_4$ alkyl, $R^1O-$, $R^1_2N-$,

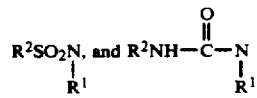

wherein $R^1$ is H, $C_1$-$C_4$ alkyl, or phenyl and $R^2$ is $C_1$-$C_4$ alkyl or phenyl; Y is hydrogen or $C_1$-$C_4$ alkyl with a proviso that when n is 0, the aryloxy group is attached to the 3 position of azetidine only;
  the stereoisomers where they exist or a pharmaceutically acceptable salt thereof.

2. The method according to claim 1 wherein the compound used is selected from:
  2-(phenoxymethyl)-1-(phenylmethyl)azetidine,
  3-[(2,6-dimethylphenoxy)methyl]-1-ethylazetidine,
  1-(1-phenylethyl)-3-[[3-(trifluoromethyl)phenoxy]-methyl]azetidine,
  1-methyl-3-phenoxyazetidine,
  3-[3-(trifluoromethyl)phenoxy]-1-[1-phenylethyl-]azetidine, 3-[3-(trifluoromethyl)phenoxy]azetidine,
3-phenoxyazetidine,
3-[(2,6-dimethylphenoxy)methyl]-1-(1-phenylethyl)azetidine,
3-[(2,6-dimethylphenoxy)methyl]azetidine,
3-[(2,6-dimethylphenoxy)azetidine,
1-ethyl-3-(2,6-dimethylphenoxy)azetidine,
3-[2-(4-aminophenoxy)ethyl]-1-(1-phenylethyl)azetidine,
N-methyl-N'-[4-[2-[1-(1-phenylethyl)-3-azetidinyl]ethoxy]phenyl]urea,
2-[(3-chlorophenoxy)propyl]-1-(1-phenylethyl)azetidine,
1-methyl-3-(4-methoxyphenoxy)azetidine,
1-(1,1-dimethylethyl)-3[(4-methylphenoxy)methyl]azetidine,
1-(1-methylethyl)-2-[(4-(phenoxy)phenoxymethyl]azetidine,
3-(4-aminophenoxy-1-ethylazetidine,
1-ethyl-3-[(4-methanesulfonylamino)phenoxy]azetidine,
a stereoisomer, or a pharmaceutically acceptable salt thereof.

3. A method of treating convulsions in warm-blooded animals which comprises administering thereto a therapeutically effective amount of a compound having the formula:

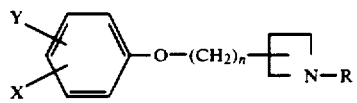

wherein n is 1 to 3, R is hydrogen, $C_1$-$C_4$ alkyl, or arylalkyl; X is selected from the group consisting of hydrogen halogen, trifluoromethyl, $C_1$-$C_4$ alkyl, $R^1O-$, $R^1_2N-$,

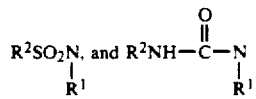

wherein $R^1$ is H, $C_1$-$C_4$ alkyl, or phenyl and $R^2$ is $C_1$-$C_4$ alkyl or phenyl; Y is hydrogen or $C_1$-$C_4$ alkyl; the stereoisomers where they exist or a pharmaceutically acceptable salt thereof.

4. The method according to claim 3 wherein the compound used is selected from:
2-(phenoxymethyl)-1-(phenylmethyl)azetidine,
3-[(2,6-dimethylphenoxy)methyl]-1-ethylazetidine,
1-(1-phenylethyl)-3-[[3-(trifluoromethyl)phenoxyl]methyl]azetidine,
3-[(2,6-dimethylphenoxy)methyl]-1-(1-phenylethyl)azetidine,
3-[(2,6-dimethylphenoxy)methyl]azetidine,
3-[2-(4-aminophenoxy)ethyl]-1-(1-phenylethyl)azetidine,
N-methyl-N'-[4-[2-[1-(1-phenylethyl)-3-azetidinyl]ethoxy]phenyl]urea,
2-[(3-chlorophenoxy)propyl]-1-(1-phenylethyl)azetidine,
1-(1,1-dimethylethyl)-3-[(4-methylphenoxy)methyl]azetidine,
1-(1-methylethyl)-2-[(4-(phenoxy)phenoxymethyl]azetidine,
a stereoisomer, or a pharmaceutically acceptable salt thereof.

5. A pharmaceutical composition for the treatment of cardiac arrhythmias or convulsions comprising (a) a therapeutically effective amount of a compound according to the formula:

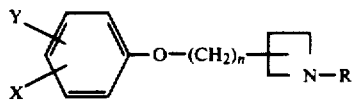

wherein n is 1 to 3, R is hydrogen, $C_1$-$C_4$ alkyl, or arylalkyl; X is selected from the group consisting of hydrogen halogen, trifluoromethyl, $C_1$-$C_4$ alkyl, $R^1O-$, $R^1_2N-$,

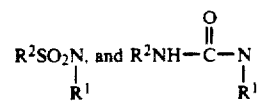

wherein $R^1$ is H, $C_1$-$C_4$ alkyl, or phenyl and $R^2$ is $C_1$-$C_4$ alkyl or phenyl; Y is hydrogen or $C_1$-$C_4$ alkyl; the stereoisomers where they exist or a pharmaceutically acceptable salt thereof, and
(b) a pharmaceutical carrier thereof.

6. A compound according to the formula:

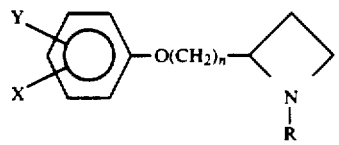

wherein n is 0 to 3, R is hydrogen, $C_1$-$C_4$ alkyl, or arylalkyl; X is selected from the group consisting of hydrogen, halogen, trifluoromethyl, $C_1$-$C_4$ alkyl, $R^1O-$, $R^1_2N-$,

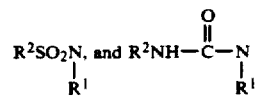

wherein $R^1$ is H, $C_1$-$C_4$ alkyl, or phenyl and $R^2$ is $C_1$-$C_4$ alkyl or phenyl; and Y is hydrogen or $C_1$-$C_4$ alkyl, a stereoisomer or a pharmaceutically acceptable salt thereof.

* * * * *